(12) United States Patent
Kwiecinski

(10) Patent No.: US 9,789,081 B2
(45) Date of Patent: Oct. 17, 2017

(54) COMPOSITIONS FOR IMPROVING SAFETY OF PHARMACOLOGICAL FORMULATIONS

(71) Applicant: Mark Kwiecinski, Ottawa (CA)

(72) Inventor: Mark Kwiecinski, Ottawa (CA)

( * ) Notice: Subject to any disclaimer, the term of this patent is extended or adjusted under 35 U.S.C. 154(b) by 0 days.

(21) Appl. No.: 15/374,385

(22) Filed: Dec. 9, 2016

(65) Prior Publication Data

US 2017/0165224 A1 Jun. 15, 2017

(51) Int. Cl.
*A61K 31/352* (2006.01)
*A61K 9/48* (2006.01)
*A61K 36/185* (2006.01)
*A61K 9/00* (2006.01)
*A61K 47/36* (2006.01)

(52) U.S. Cl.
CPC .......... *A61K 31/352* (2013.01); *A61K 9/0004* (2013.01); *A61K 9/009* (2013.01); *A61K 9/0078* (2013.01); *A61K 9/4866* (2013.01); *A61K 36/185* (2013.01); *A61K 47/36* (2013.01)

(58) Field of Classification Search
None
See application file for complete search history.

(56) References Cited

FOREIGN PATENT DOCUMENTS

WO 2008/033024 * 3/2008
WO 2013/169101 * 11/2013

* cited by examiner

*Primary Examiner* — Karl J Puttlitz
(74) *Attorney, Agent, or Firm* — Shapiro Cohen LLP

(57) ABSTRACT

Disclosed are compositions for improving the safety of pharmaceutical formulations. These compositions include additives for limiting the bioavailability of the active ingredient of a pharmaceutical composition when administered to a subject in a manner other than originally intended.

11 Claims, 2 Drawing Sheets

COMPOSITIONS FOR IMPROVING SAFETY OF PHARMACOLOGICAL FORMULATIONS

FIELD OF THE INVENTION

The present invention generally relates to compositions for improving the safety of pharmaceutical formulations. More specifically, the present invention relates to additives for limiting the bioavailability of the active ingredient of a pharmaceutical composition when administered to a subject in a manner other than originally intended.

BACKGROUND

Reports indicate that medicinal marijuana may be used to treat a variety of symptoms related to disease. Marijuana has been shown to be an effective treatment for: chronic pain associated fibromyalgia and rheumatoid arthritis; chemotherapy-induced nausea and vomiting; neurological problems such as epilepsy, multiple sclerosis, other types of muscle spasms, and Parkinson's disease; anorexia from chemotherapy or other diseases; anxiety, depression; post traumatic stress disorder (PTSD); insomnia; and, symptoms in patients diagnosed with Acquired Immunodeficiency Syndrome (AIDS), inflammatory bowel disease and Crohn's disease.

Recent legalization of medicinal marijuana, or medicinal cannabis, in countries such as Canada, Australia, and the United Kingdom, as well as in some states in the U.S.A., has increased the presence of this pharmaceutical in homes. As such, instances of accidental ingestion of this medicinal product, especially by children, have been on the rise. The deleterious effects in children are typically more serious as THC concentration in medicinal marijuana are generally higher than found in marijuana used for recreational purposes. For example, in severe circumstances, children that accidentally ingested cannabis have required assisted ventilation or have even entered into a coma as described in Macnab, A. Anderson, E and Susak, L. "Ingestion of cannabis: A cause of coma in children." Pediatric emergency care 5.4 (1989):238-239).

Other medications also pose a risk to those with access. As the population ages, more medication is available in more medicine cabinets and prone to intentional or accidental misuse. This has become quite problematic, with a large number of illnesses and overdoses related to inappropriate prescription drug use other than by the intended patient or other than as instructed.

It is desirable to develop a composition that can limit bioavailability of some medical ingredients, such as tetrahydrocannabinol, when the composition comes into contact with a subject in a manner other than originally intended.

SUMMARY OF THE INVENTION

According to an aspect of the present invention, there is provided a pharmaceutical composition comprising an active ingredient and a sugar polyester.

In one embodiment, the active ingredient is derived from a cannabis plant or a synthetic compound thereof. In particular, the active ingredient is one or more cannabinoids, such as tetrahydrocannabinol.

In another embodiment, the sugar polyester is olestra.

In a further embodiment, the tetrahydrocannabinol in the composition is present in an amount of from about 10 to about 50 wt % and/or the sugar polyester is present in an amount of from about 65 to about 85 wt %.

In a still further embodiment, the active ingredient: sugar polyester ratio is about 1:6 to about 1:3 by weight In an embodiment, the composition further comprises additives, such as propylene glycol, glycerin, water, nicotine, flavorings, or combinations thereof.

In another embodiment, the composition is for use in a vaporizer.

In a still further embodiment, the composition is hydrophobic and lipophilic.

According to another aspect of the present invention, there is provided the use of the pharmaceutical composition described above for limiting the bioavailability of the active ingredient when administered to a subject via a route of administration other than originally intended.

In one embodiment, the pharmaceutical composition is for use in a vaporizer.

In accordance with another aspect of the invention, there is provided a pharmaceutical composition comprising an active ingredient, the composition and a sugar polyester portion removably disposed therewith, the sugar polyester portion for being removed from the composition prior to administration thereof.

In one embodiment, the sugar polyester forms part of a removable casing.

In another embodiment, the sugar polyester forms an extractable portion of the composition.

In yet another embodiment, the sugar polyester forms a neutralizable portion of the composition for being neutralized prior to administration of the composition.

DETAILED DESCRIPTION

Figure 1:
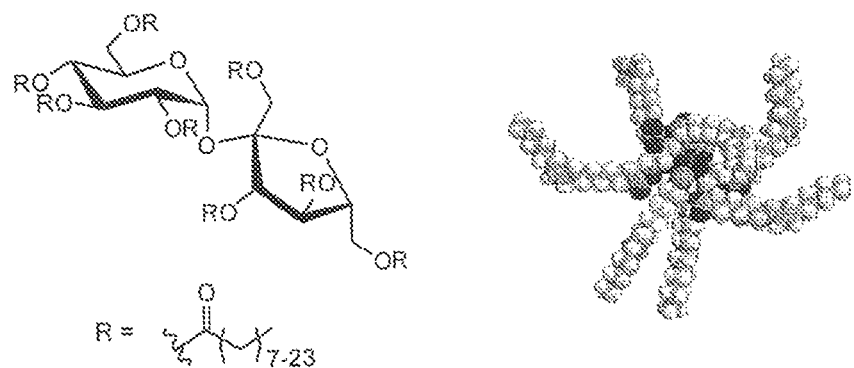
FIG. 1 is a chemical diagram.

Described herein are embodiments of pharmaceutical and a sugar polyester for limiting the bioavailability of the pharmaceutical when administered other than as intended. In an embodiment, the pharmaceutical functions as intended when administered in one fashion but is less functional or inert when administered in another fashion. In another embodiment, the pharmaceutical functions as intended only if pre-processed; otherwise it is less functional or inert. In yet another embodiment, the function of the pharmaceutical is varied through preprocessing thereof.

In a first embodiment, the pharmaceutical composition comprises an active ingredient and a sugar polyester. The composition is useful for limiting the bioavailability of the active ingredient when administered to a subject via a route of administration other than originally intended. It will be appreciated that the embodiments and examples described herein are for illustrative purposes and are intended for those skilled in the art and are not meant to be limiting. All references to embodiments or examples throughout the disclosure should be considered a reference to an illustrative and non-limiting embodiment or an illustrative and non-limiting example.

According to an embodiment of the present invention, there is provided a pharmacological composition comprising an active ingredient and a sugar polyester. In one embodiment, the pharmaceutical composition is hydrophobic and lipophilic. The compositions of the present invention prevent or limit the active ingredient from having its intended or normal physiological and/or psychological effect on the subject that comes into contact with—administers—the composition in a manner other than what was originally intended. For example, a hydrophobic and lipophilic pharmacological composition comprising cannabinoids as the active ingredient and olestra as the sugar polyester would be intended to be used in a vaporizer, or burned, for inhalation by the user.

The physiological and psychological effect of the active ingredient (i.e. bioavailability) would be achieved via this route of administration. In contrast, if a subject were to be exposed to the composition via ingestion, topically, injection or any other route of administration other than what was originally intended, the physiological and psychological effect of the active ingredient would either not be experienced or would be limited relative to the intended effects. For the purposes of this description, the term "subject" means any living organism that would be physiologically or psychologically affected by the active ingredient.

The sugar polyesters of the present invention are sugar fatty acid esters esterified with at least six fatty acid groups, preferably six, seven or eight fatty acid groups. The term "sugar" is used herein in its conventional sense as generic to mono-, di-, and trisaccharides. The fatty acid ester compounds are prepared by reacting a monosaccharide, disaccharide or trisaccharide with fatty acid as would known in the art.

Examples-of—suitable monosaccharides are those containing 4 hydroxyl groups such as xylose, arabinose, and ribose. The monosaccharide erythrose may not be suitable for the practice of this invention as it only contains 3 hydroxyl groups. Among 5 hydroxyl containing monosaccharides that are suitable for use herein are glucose, mannose, galactose, fructose, and sorbose. Examples of suitable disaccharides are maltose, lactose, and sucrose, all of which contain 8 hydroxyl groups. Examples of suitable trisaccharides are maltotriose and raffinose. The exemplary embodiments described for cannabanoids rely on sucrose for preparing the polyesters for use.

In the context of the present invention, the sugar polyester is a substance that is not internalized by the digestive tract in a human. One such, non-limiting example of a sucrose polyester is olestra. However, other sugar polyesters capable of interacting with an active ingredient and preventing that active ingredient from being absorbed through the digestive tract are also considered as suitable options when their effects on the digestive system and the subject are considered and any effects they may have when ingested as intended.

The structure of olestra comprises a sucrose disaccharide esterified with long fatty acid chains as shown in FIG. 1. It has been suggested that steric hindrance due to the long fatty acid chains prevents hydrolysis of the esters by enzymes as described in Rattagool, K. Scientific Considerations of Olestra as a Fat Substitute. Master of Science, University of North Texas, Denton, Tex. December 1999. The inability of olestra to be broken down prevents its absorption though the epithelial cells of the digestive tract. Olestra interferes with the absorption of other lipophilic molecules, such as fat-soluble vitamins. This is due to the partition of these molecules into the non-absorbable olestra, which then carries the molecules out of the body as described in Lawson, K D., Middleton, S. J., and Hassal,l C. D. "Olestra, a nonabsorbed, noncaloric replacement for dietary fat: a review." Drug metabolism reviews 29.3 (1997): 651-703. In fact, when olestra was approved for human consumption, it was specified that food containing olestra had to be fortified with fat soluble vitamins to replace the vitamins that were stripped from the body of the consumer. In the context the present invention without being limited by theory olestra may interact with hydrophobic active ingredients and prevent their absorption by the digestive system.

In a non-limiting embodiment of the present invention, the active ingredient is derived from a cannabis plant, such as from the species sativa, indica and ruderalis. Cannabinoids derived from cannabis plants, or synthetic cannabinoids, are responsible for the psychotropic effects experienced after a subject is administered the cannabis plants or parts thereof, and are contemplated for use in the present invention.

Figure 2:
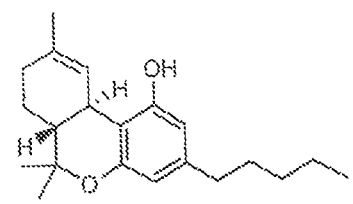
FIG. 2 is a chemical diagram.

In a further embodiment, the active ingredient comprises tetrahydrocannabinol (THC), the principle psychoactive constituent of cannabis, which is reported to be partly associated with the medical benefits of marijuana. The structure of THC is illustrated in FIG. 2. Without being limited by theory, THC is oil-soluble and therefore may interact with large sucrose polyesters and resist absorption by the digestive system when orally ingested. Depending on the strain of cannabis or the extraction method, cannabis oil may comprise a varying amount of THC. In one embodiment of the composition, THC is present in an amount of from 10 to about 50 wt %, preferably about 10 to about 50 wt %, with about 5 to about 10 wt % being other cannabis compounds.

In an embodiment of the composition, the sugar polyester in the composition is present in an amount of from about 65 to about 85 wt %. In one embodiment, the active ingredient: sugar polyester ratio in the pharmaceutical composition is about 1:6 to about 1:3 by weight. In an even further embodiment, the active ingredient: sugar polyester ratio is about 1:1 by weight.

In some embodiments of the composition, additives are included, for example, propylene glycol, glycerin, water, nicotine, flavorings, or combinations thereof. Other additives known in the art may also be included in the composition.

In liquid form, the active ingredient, for example THC and other cannabinoids, interacts with the sugar polyester, such as olestra, and passes through the digestive system unabsorbed. However, when the composition is heated, through vaporization or combustion, the active ingredients will be released as they are converted into a gas or vapor while olestra will remain as a solid, as it is a non-volatile compound. Therefore, accidental oral consumption of the composition is unlikely to result in harmful effects or substantial other effects associated with the absorption of the active ingredient. The active ingredient may be absorbed by inhalation of a vapor or smoke produced by heating the composition at a temperature of approximately 150 to 220° C. The vapour and resulting smoke may be produced by any means know in the art, such as a vaporizer or through burning.

Figure 3:
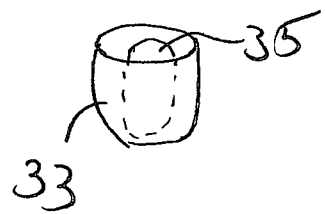
FIG. 3 is a diagram of a pouch.

Referring to FIG. 3, shown is a pouch 33 for containing an active ingredient in the form of pill 35. The pouch 33 is filled with a sugar polyester for encasing the pill. If ingested, the sugar polyester buffers effects of the active ingredient by absorbing at least some of the active ingredient to prevent activation thereof. In accordance with instructions for use, the pouch 33 is removed prior to ingestion of the pill 35 to render the active ingredient as effective as intended. Thus, effects of accidental consumption or consumption by a child can often be mitigated.

Figure 4:
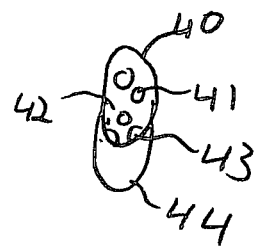
FIG. 4 is a diagram of a filter mechanism.

Referring to FIG. 4, shown is another embodiment wherein the medicine comprises an active ingredient 41 and a sugar polyester 42 mixed together. Here particle sizes of each of the active ingredient 41 and the sugar polyester 42 are distinct and a screen 43 allows for separation of the active ingredient from the sugar polyester. Thus, the active ingredient can be ingested in isolation for intended use, but the medicine requires processing in order to be fully bioavailable. As shown in FIG. 4, the screen forms part of a capsule allowing the sugar polyester to be removed by tilting the capsule and shaking it once the end 44 is broken off. Then the capsule 40 can be swallowed as intended. Of course, once separated, ingestion of the active ingredient is according to an indicated method of consumption.

Figure 5:
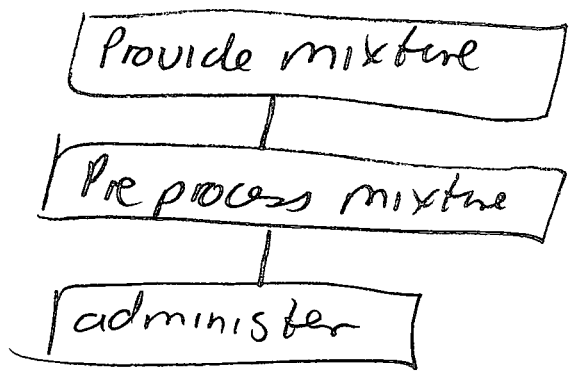
FIG. 5 is a simplified flow diagram of a method according to an embodiment of the invention.

Referring to FIG. 5, shown is a simplified flow diagram of another embodiment wherein the medicine comprises an active ingredient 41 and a sugar polyester 42 mixed together. Here a process is employed to neutralize the sugar polyester and its limiting function. For example, the medicine is added to liquid for dissolving and neutralizing the sugar polyester. Such a system is useful for neutralizing the sugar polyester or for partially neutralizing same. When used to partially neutralize the sugar polyester, the effects of the medicinal ingredient can be moderated using the sugar polyester as a moderating agent; the amount of sugar polyester neutralized indicated the effectiveness of the overall medicine dose.

In another embodiment, the active ingredient (A) is combined with a neutralizing agent (B), such that the combined mixture is pharmaceutically inactive. In this embodiment, A and B have a different solubility in sugar polyester (C), such that the neutralizing agent is taken up and immobilized in the sugar polyester (C) to a higher degree than the active pharmaceutical, resulting in some pharmaceutically active A being liberated. In this way, while A+B together has no pharmaceutical effect, the resultant mixture of A+B+C is at least partially pharmaceutically active.

Though the embodiments are described with reference to cannabinoids, many pharmaceutical compositions are soluble in a sugar polyester and the present embodiments apply to those pharmaceutical compositions. For example, Fentanyl is known to be lipid soluble as are many prescription drugs.

Various embodiments of hydrophobic and lipophilic pharmaceutical compositions comprising an active ingredient and a sugar polyester have been described. The above-described embodiments are intended to be examples and alterations and modifications may be effected thereto by those of skill in the art, without departing from the scope of the teachings.

What is claimed is:

1. A pharmaceutical composition comprising tetrahydrocannabinol and a sugar polyester, wherein said sugar polyester is a mono-, di-, or trisaccharide esterified with at least 6 fatty acid groups.

2. The pharmaceutical composition of claim 1, wherein the sugar polyester is olestra.

3. The pharmaceutical composition of claim 1, wherein the tetrahydrocannabinol in the composition is present in an amount of from about 10 to about 50 wt %.

4. The pharmaceutical composition of claim 3, wherein the sugar polyester is present in an amount of from about 65 to about 85 wt %.

5. The pharmaceutical composition of claim 2, wherein the tetrahydrocannabinol to sugar polyester ratio is about 1:6 to about 1:3 by weight.

6. The pharmaceutical composition of claim 1, comprising additives, wherein the additives are propylene glycol, glycerin, water, nicotine, flavorings, or combinations thereof.

7. The pharmaceutical composition of claim 1, wherein the composition is for use in a vaporizer.

8. The pharmaceutical composition of claim 1, the composition being hydrophobic and lipophilic.

9. The pharmaceutical composition of claim 1, wherein the mixture allows for separation of the tetrahydrocannabinol and the sugar polyester prior to use thereof.

10. The composition of claim 9 wherein granules of the tetrahydrocannabinol are a different and distinguishable size from granules of the sugar polyester.

11. A composition according to claim 10 wherein administration of the composition is less effective than administration of tetrahydrocannabinol separated from the mixture.

* * * * *

UNITED STATES PATENT AND TRADEMARK OFFICE
CERTIFICATE OF CORRECTION

PATENT NO. : 9,789,081 B2
APPLICATION NO. : 15/374385
DATED : October 17, 2017
INVENTOR(S) : Mark Kwiecinski Page 1 of 1

It is certified that error appears in the above-identified patent and that said Letters Patent is hereby corrected as shown below:

On the Title Page

Between item (65) and item (51) insert:
--(30) Foreign Application Priority Data:
Dec. 9, 2015 (CA)..........................2914611--

Signed and Sealed this
Tenth Day of July, 2018

Andrei Iancu
*Director of the United States Patent and Trademark Office*